United States Patent [19]

Shubair

[11] Patent Number: 5,122,366
[45] Date of Patent: Jun. 16, 1992

[54] ANTISMOKE MOUTH WASH COMPRISING SILVER NITRATE AND PROPYLENE GLYCOL

[75] Inventor: Mohammed S. S. Shubair, Salt, Jordan

[73] Assignee: The Arab Pharmaceutical Company, Salt, Jordan

[21] Appl. No.: 412,135

[22] Filed: Sep. 25, 1989

[30] Foreign Application Priority Data

Jan. 21, 1989 [JO] Jordan .................................... 1560

[51] Int. Cl.$^5$ ...................... A61K 33/38; A24F 47/00
[52] U.S. Cl. ...................................... 424/49; 424/618; 514/813; 514/901; 131/270
[58] Field of Search .................. 424/618, 49; 514/813, 514/901; 131/270

[56] References Cited

U.S. PATENT DOCUMENTS

| | | | |
|---|---|---|---|
| 3,071,509 | 1/1963 | O'Neill | 131/270 |
| 4,311,691 | 1/1982 | Fichera | 426/548 |
| 4,627,980 | 12/1986 | Lynch | 424/49 |
| 4,747,417 | 9/1988 | Beskin | 131/270 |
| 4,867,181 | 9/1989 | Smolko | 131/329 |
| 4,951,691 | 8/1990 | Leary | 131/270 |
| 4,971,079 | 11/1990 | Talapin et al. | 131/270 |

FOREIGN PATENT DOCUMENTS

| | | | |
|---|---|---|---|
| 2747500 | 4/1979 | Fed. Rep. of Germany | 131/270 |
| 2242039 | 3/1975 | France | 131/270 |

Primary Examiner—Ronald W. Griffin
Attorney, Agent, or Firm—Ladas & Parry

[57] ABSTRACT

An antismoke mouthwash comprising silver nitrate and propylene glycol in water, a process for preparing said mouthwash and a method of using the mouthwash to help a smoker quit smoking.

7 Claims, No Drawings

ANTISMOKE MOUTH WASH COMPRISING SILVER NITRATE AND PROPYLENE GLYCOL

Smoking is one of the major causes of death. Many dangerous diseases are associated with cigarette smoking, such as, cancer of the lung; cancers of the upper respiratory and digestive tracts; chronic bronchitis; Pulmonary tuberculosis; peptic ulcer, cirrhosis of the liver, coronary disease without hypertension (1).

(1) LAURENCE, Clinical Pharmacology, 1977, 4th Edition, 13.17, Churchill Livingstone Most of the products used as antismoking are based on the presence of nicotine or tobacco with other Ingredients such as oils in the form of chewing gums or lozenges.

Silver nitrate has unique astringent and bitter properties and Interact with nicotine to produce nicotinic acid and unpleasant taste stopping the smoker from continuing to smoke, such deterrent effect to smoking is increased by any attempt to continue smoking.

Silver nitrate is incompatibile with organic and most inorganic materials as well as packaging materials (2, 3).

(2) Remington Pharmaceutical Sciences, 17th, Edition, Mack Puplication co, 1985
(3) Martindale, Extra Pharmacopoeia, 28th, Edition, Pharmaceutical Press, 1982

No attempt was made to formulate silver nitrate in a stable solution form as mouthwash although it is safe due to inabsorbability of silver protein formed when the mouth washed with silver nitrate solution.

Recently, while this project in progress, a British Company M & D Marketing consultancy registered a patent for a product called: "Givup mouth wash" contains silver acetate 0.2%, such product is less effective than the silver nitrate.

ANTISMOKE MOUTHWASH

| Ingredients | Qty/Liter |
| --- | --- |
| Silver Nitrate | 5 gm. |
| Propylene Glycol | 20 gm. |
| Cough Flavour* | 0.5 ml. |
| Distilled Water up to | 1000 ml. |

METHOD OF PREPARATION

Dissolve Silver Nitrate in about 700 ml. distilled water.

Add Propylene Glycol or glycerin and mix for 5 minutes.

Add cough flavour and mix for 10 minutes.

Add the required quantity of distilled water and mix for 10 minutes.

Fill into bottles with the following specification.

SPECIFICATIONS OF PACKAGING

Bottle: made of amber colour high density polyvinyl chloride.

Cap: made of brown colour high density polyethylene.

Internal Plug: made of brown colour low density polyethylene.

Ring: made of brown colour low density polyethylene.

Dosage: Fill the Cap with the solution and rinse the mouth for 2 minutes 3 times daily after meal.

What we claim is:

1. A stable mouthwash composition comprising silver nitrate and propylene glycol in aqueous solution.

2. A stable mouthwash composition comprising silver nitrate and propylene glycol in aqueous solution said composition not containing nitric acid.

3. A mouthwash according to claim 1 further comprising flavors.

4. A composition according to claim 1 wherein the concentration of silver nitrate is 0.5%.

5. A mouthwash composition according to claim 1, which comprises,
   0.5%—silver nitrate
   2%—propylene glycol
   0.05%—cough flavor and sufficient distilled water to make up to 100 ml.

6. A process for preparing a stable mouthwash composition comprising:
   dissolving silver nitrate in 70% of the total desired quantity of water;
   adding propylene glycol and mixing solution for 5 minutes;
   adding the remainder of the desired quantity of water and mixing the solution for ten minutes.

7. A method to aid a smoker quit smoking comprising rinsing with a mouthwash comprising silver nitrate and propylene glycol said rinsing occurring three times daily.

* * * * *